United States Patent
Zhang

(10) Patent No.: US 11,294,010 B2
(45) Date of Patent: Apr. 5, 2022

(54) METHOD AND APPARATUS FOR DETERMINING OPTIMAL MAGNETIC RESONANCE IMAGING SCAN NESTING MANNER

(71) Applicant: Siemens Healthcare GmbH, Erlangen (DE)

(72) Inventor: Qiong Zhang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 75 days.

(21) Appl. No.: 16/555,389

(22) Filed: Aug. 29, 2019

(65) Prior Publication Data

US 2020/0072930 A1   Mar. 5, 2020

(30) Foreign Application Priority Data

Aug. 29, 2018  (CN) .......................... 201810992601.3

(51) Int. Cl.
*G01R 33/483* (2006.01)
*A61B 5/055* (2006.01)
(Continued)

(52) U.S. Cl.
CPC .......... *G01R 33/4835* (2013.01); *A61B 5/055* (2013.01); *G01R 33/50* (2013.01); *G01R 33/546* (2013.01); *G01R 33/543* (2013.01)

(58) Field of Classification Search
CPC .. G01R 33/4835; G01R 33/50; G01R 33/543; G01R 33/546; A61B 5/055
See application file for complete search history.

(56) References Cited

U.S. PATENT DOCUMENTS 4,673,880 A   6/1987  Compton et al.
5,406,203 A   4/1995  Oh et al.
(Continued)

FOREIGN PATENT DOCUMENTS

CN       1147639 A      4/1997
CN     102772206 A     11/2012
(Continued)

OTHER PUBLICATIONS

Wang et al., "The Effective Connectivity of Resting State Functional MRI and its Application in Bipolar Disorder," China Outstanding Master's Degree Thesis Full Text Database-Medicine and Health Science and Technology Series; Issue 11 E080-17 (2013); English-language abstract included.
(Continued)

*Primary Examiner* — Gregory H Curran
(74) *Attorney, Agent, or Firm* — Schiff Hardin LLP

(57) ABSTRACT

In a method and system for determining an optimal MRI scan nesting manner, selectable nesting manners are determined according to a preset number of simulated scan slices; one nesting manner from all the selectable nesting manners is sequentially selected; based on the selected nesting manner, a simulated MRI scan is performed using a preset pulse sequence, and a longitudinal magnetization strength after relaxation of each slice when scanning ends is calculated; when all nesting manners have been selected, based on the longitudinal magnetization strength after relaxation of each slice when scanning ends corresponding to each nesting manner, a nesting manner for which the longitudinal magnetization strength after relaxation is smoothest is selected, and the nesting manner is used as an optimal nesting manner for performing an MRI scan of the tissue.

15 Claims, 7 Drawing Sheets

(51) Int. Cl.
*G01R 33/50* (2006.01)
*G01R 33/54* (2006.01)

(56) References Cited

U.S. PATENT DOCUMENTS

| | | | |
|---|---|---|---|
| 5,751,145 | A | 5/1998 | Shimizu |
| 8,803,523 | B2 | 8/2014 | Hargreaves |
| 10,061,007 | B2 | 8/2018 | Gui et al. |
| 10,114,096 | B2 | 10/2018 | Liu et al. |
| 2010/0136929 | A1* | 6/2010 | Vernickel ......... G01R 33/34076 455/91 |
| 2013/0200892 | A1 | 8/2013 | Hargreaves |
| 2014/0152304 | A1* | 6/2014 | Fielden ................ G01R 33/565 324/309 |
| 2015/0377994 | A1 | 12/2015 | Gui et al. |
| 2016/0178719 | A1 | 6/2016 | Liu et al. |

FOREIGN PATENT DOCUMENTS

| | | |
|---|---|---|
| CN | 103239230 A | 8/2013 |
| CN | 104224179 A | 12/2014 |
| CN | 105785297 A | 7/2016 |
| CN | 106198597 A | 12/2016 |
| CN | 107271937 A | 10/2017 |
| CN | 108209918 A | 6/2018 |
| EP | 0284284 A2 | 9/1988 |
| JP | S6243549 A | 2/1987 |
| JP | 2016189979 A | 11/2016 |
| RU | 2613083 C1 | 3/2017 |

OTHER PUBLICATIONS

Mengyue et al., "MRI artifacts in body imaging and Countermeasures," Radiology Practice, vol. 31, pp. 141-144 (2016); English-language machine translation attached.

Weiping et al., "MRI Technology and Experimentation," Jiangsu University Press, pp. 35-45 (2018); English-language machine translation attached.

Yexin et al., "The countermeasures of the artifacts in MRI imaging," Basic Medical Forum, vol. 20, pp. 3548-3550 (2016); English-language machine translation attached.

Chinese Office Action dated Jun. 30, 2021 (English-language machine translation attached).

Takashi Sakai et al.: "Simulation Analysis of Multislice Profiles in MRI Based on Bloch Equation"; Medical Imaging and Information Sciences; vo 1.23, No. 3, Jan. 1, 2006 (Jan. 1, 2006), pp. 100-104; XP055656269; ISSN : 0910-1543; 2006.

Liu, Wei et al. "An Optimized Slice Acquisition Order in HASTE Imaging with a Short TR" Proceedings of the International Society for Magnetic Resonance in Medicine (ISMRM 2016), 24th Annual Meeting & Exhibition; Abstract No. 1808, Apr. 22, 2016.

Bernstein, Matt A. et al. "Handbook of MRI Pulse Sequences" Chapter 11.5.2. Cross-Talk and Slice Ordering, Elsevier Academic Press, Amsterdam, pp. 410-415, 2004.

E.Mark Haacke, Robert W.Brown,et,al. Bloch equation and static-field solutions,Magnetic Resonance Imaging, physical principles and sequence design, p. 60-p. 62,2007; 2007.

Jung-Jiin Hsu. Flip-angle profile of slice-selective excitation and the measurement of the MR longitudinal relaxation time with steady-state magnetization. Physics in Medicine and Biology, V60, N15,2015; 2015.

European Search Report dated Jan. 23, 2020, Application No. 19194033.7.

* cited by examiner

METHOD AND APPARATUS FOR DETERMINING OPTIMAL MAGNETIC RESONANCE IMAGING SCAN NESTING MANNER

CROSS REFERENCE TO RELATED APPLICATIONS

This patent application claims priority to Chinese Patent Application No. 201810992601.3, filed Aug. 29, 2018, which is incorporated herein by reference in its entirety.

BACKGROUND

Field

The present disclosure relates to the technical field of MRI (magnetic resonance imaging), in particular to a method and apparatus for determining an optimal MRI scan nesting manner, and a readable storage medium.

Related Art

In MRI, a radio frequency (RF) pulse of a specific frequency is applied to a human body in a static magnetic field, such that hydrogen protons in the human body are excited and experience the phenomenon of magnetic resonance. When the pulse is stopped, the protons give rise to MR (magnetic resonance) signals in the course of relaxation. An MR image is created by processing such as MR signal reception, spatial encoding and image reconstruction.

Commonly used MRI scan pulse sequences are as follows:

1. SE (Spin-Echo sequence): First of all a 90° excitation pulse is emitted, then a 180° phase refocusing pulse is emitted after an interval of a few milliseconds to a few tens of milliseconds, then an echo signal is measured after a few tens of milliseconds. Thus, there is only one 180° pulse in one TR (repetition time). This is called a spin echo sequence (SE), and is a classic sequence in MR imaging. There are three types of weighted imaging with an SE sequence:

A. PD (proton density) weighted image
  Parameters: long TR=1500-2500 ms, short TE (echo time)=15-30 ms; the amplitude of the echo signal acquired is mainly related to proton density, so this type of image is called a PD weighted image.

B. T2 (transverse relaxation time) weighted image
  Parameters: long TR=1500-2500 ms, long TE=90-120 ms; the amplitude of the echo signal acquired mainly reflects differences in the T2 of tissues, so this type of image is called a T2 weighted image.

C. T1 (longitudinal relaxation time) weighted image
  Parameters: short TR=about 500 ms, short TE=15-30 ms; the amplitude of the echo signal acquired mainly reflects differences in the T1 of tissues, so this type of image is called a T1 weighted image.

2. TSE (Turbo Spin-Echo sequence): a sequence established on the basis of an SE sequence. First of all a 90° excitation pulse is emitted, then multiple 180° phase refocusing pulses in the same direction are emitted, to form an echo train (ETL, Echo Train Length), thereby shortening the scan time. This is called a turbo spin echo sequence (TSE).

HASTE (Half-Fourier Acquisition Single-shot Turbo spin-Echo sequence) is one type of TSE sequence, distinctive in being a single-excitation rapid imaging sequence, with a scan time that is reduced by half.

3. GRE (Gradient-Echo sequence): This is MR imaging using gradient echo. Gradient echo is similar to spin echo. The generation of a spin echo uses a 180° complex phase pulse. With regard to gradient echo generation, forward/reverse switching of the readout gradient field direction is used after one RF excitation to generate a gradient echo.

4. EPI (Echo Planar Imaging): currently the fastest sequence in MR imaging; the MR signal is also a gradient echo. Unlike ordinary gradient echo, after one RF excitation, successive forward/reverse switching of the readout gradient field is utilized, and one gradient echo is generated each time switching is performed, therefore there is an echo train, similar to TSE.

TR is the time needed for a pulse sequence to be executed once. In SE, TR is the time interval between the mid-points of two adjacent 90° pulses; in GRE, TR is the time interval between the mid-points of two adjacent small-angle pulses.

Regarding effective TE (Echo Time), in a TSE or EPI sequence, multiple echoes are generated after one 90° pulse excitation, and respectively used to fill different positions of k-space, with each echo having a different TE; in these sequences, the time interval from the mid-point of a 90° pulse to the mid-point of the echo used to fill the center of k-space is called the effective TE.

ETL (Echo Train Length) appears in a TSE or EPI sequence. It is the number of echoes generated or acquired after one 90° pulse excitation.

Under the action of an RF pulse, the macroscopic magnetization vector of tissue will deviate from an equilibrium state (i.e. the B0 direction); the angle of deviation thereof is called the flip angle. The flip angle of the macroscopic magnetization vector depends on the energy of the RF pulse; the greater the energy, the greater the flip angle. The energy of the RF pulse depends on the intensity and duration of the pulse, so an increase in energy can be achieved by increasing the intensity or/and duration of the pulse. Flip angles commonly used in MRI are 90°, 180° and small angles commonly used in GRE sequences.

A general principle of thermodynamics is that all systems tend towards their own lowest energy states. In the phenomenon of nuclear magnetic resonance, relaxation is a phenomenon whereby, when an atomic nucleus experiences resonance and is in a high-energy state, it will rapidly recover to an original low-energy state after an RF pulse stops. The process of recovery is called the relaxation process, which is an energy conversion process, and the fact that a certain time is needed reflects the interaction between protons in the proton system and between protons and the surrounding environment.

The completion of the relaxation process takes place in two steps, i.e. the recovery of the longitudinal magnetization strength vector Mz to M0 of an initial equilibrium state, and the attenuation of the transverse magnetization strength Mxy to zero; these two steps begin at the same time but are completed independently.

The T1 relaxation time describes the speed at which the two-energy-level population in the spin system goes to thermal equilibrium from the start.

The speed at which the longitudinal magnetization strength component Mz recovers to M0 of the equilibrium state is directly proportional to the extent to which they leave an equilibrium position; when the 90° pulse has acted, an expression for the recovery of the longitudinal magnetization strength Mz can be obtained:

$$Mz(t)=M0(1-e^{-t/T1})$$

T1 in the formula above is the longitudinal relaxation time, abbreviated as T1; generally, the time needed for Mz to recover from zero to 63% of M0 is used to determine T1, i.e. the longitudinal relaxation time T1 is the time needed for Mz to recover to 0.63 M0, and t is the length of time from the moment that relaxation began to the current moment.

The size of the longitudinal relaxation time T1 depends on the external magnetic field and the interaction between protons and the surrounding environment (i.e. the nature of the tissue). It is an intrinsic characteristic of tissue; for a given external magnetic field, the T1 values of different tissues all have corresponding fixed values, but there is wide variation in the T1 values of different tissues. The external magnetic field B0 (the size of B0) also has an influence on the longitudinal relaxation time T1 of tissue; the longitudinal relaxation time T1 of most tissues decreases as the external magnetic field B0 decreases. However, this is not true in the case of pure water (also called free water); the T1 value thereof does not change as the strength of the external magnetic field changes.

The slice thickness in MRI is determined by the slice selection gradient field strength and the RF pulse width; in 2D images, the slice thickness is the thickness of the excited slice. The thinner the slice thickness, the higher the spatial resolution of the image in the slice selection direction, but due to the decrease in voxel volume, the image signal-to-noise ratio is reduced. Thus, when selecting the slice thickness, account must be taken of not only the spatial resolution but also the image signal-to-noise ratio.

The distance between two adjacent slices is the slice separation. During MRI imaging, tissue between two slices is not imaged, for example: if the slice thickness is 25 px and the slice separation is 12.5 px, then tissue with a thickness of 12.5 px between two slices is not imaged. MR slice imaging is realized by means of selective RF pulses; due to the influence of gradient field linearity and RF pulse frequency characteristics, etc., protons near a scanned slice will in fact also be excited, and this will result in signals affecting each other between slices; this effect is called inter-slice interference or inter-slice contamination.

In order to reduce inter-slice interference, the following two methods are generally used:

Method 1: introducing a 10-30% slice separation between adjacent slices, so that "tails" of echo signals of adjacent slices do not overlap.

Method 2: scanning in a nested manner. That is, when scanning is performed, it is not performed sequentially in the order of slices, but performed in a nested manner. The incremental number of slices in nesting may be one slice or multiple slices. For example, slices are numbered sequentially as slices 1, 2, 3, . . . , n according to the positions of the slices in tissue. Then:

If scanning is performed in a nested manner with the incremental number of slices being one slice, then the scanned slices are sequentially: slices 1, 2, 3, 4, 5, 6, . . . ;

If scanning is performed in a nested manner with the incremental number of slices being two slices, then the scanned slices are sequentially: slices 1, 3, 5, 7, . . . , 2, 4, 6, 8, . . . ;

If scanning is performed in a nested manner with the incremental number of slices being three slices, then the scanned slices are sequentially: slices 1, 4, 7, 10, . . . , 2, 5, 8, 11, . . . , 3, 6, 9, 12, . . . ;

If scanning is performed in a nested manner with the incremental number of slices being four slices, then the scanned slices are sequentially: slices 1, 5, 9, 13, . . . , 2, 6, 10, 14, . . . , 3, 7, 11, 15, . . . , 4, 8, 12, 16, . . .

At the present time, when scanning is performed in a nested manner, the incremental number of slices is generally determined based on experience, and as a result, it cannot be ensured that an optimal manner of nesting is used, i.e. that an optimal MRI imaging result is obtained.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
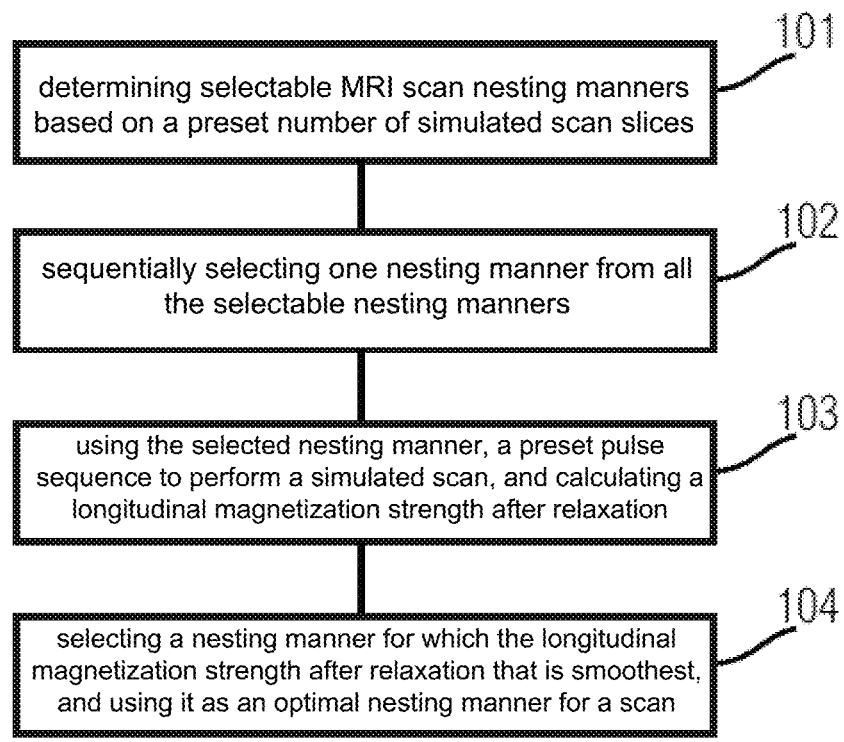
FIG. 1 is a flow chart of a method for determining an optimal MRI scan nesting manner according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to provide a method for determining an optimal MRI scan nesting manner, in order to find an optimal MRI scan nesting manner.

Another object is to provide an apparatus for determining an optimal MRI scan nesting manner, in order to find an optimal MRI scan nesting manner.

Another object is to provide a readable storage medium, in order to find an optimal MRI scan nesting manner.

In an exemplary embodiment, a method for determining an optimal magnetic resonance imaging (MRI) scan nesting manner, includes: determining all selectable nesting manners according to a preset number of simulated scan slices; sequentially selecting one nesting manner from all the selectable nesting manners; using the selected nesting manner, using a preset pulse sequence to perform a simulated MRI scan of a set tissue, and calculating a longitudinal magnetization strength after relaxation of each slice when scanning ends; when all nesting manners have been selected, then based on the longitudinal magnetization strength after relaxation of each slice when scanning ends corresponding to each nesting manner, selecting a nesting manner for which the longitudinal magnetization strength after relaxation is smoothest, and using this nesting manner as an optimal nesting manner for performing an MRI scan of the tissue.

In an exemplary embodiment, the determining all the selectable nesting manners includes: calculating M=⌊total number of scan slices/2⌋, where ⌊ ⌋ is a symbol for rounding down operation. Here, there are a total of M selectable nesting manners, where the smallest incremental number of slices corresponding to a selectable nesting manner=1, and the largest incremental number of slices=M.

In an exemplary embodiment, the selecting the nesting manner for which the longitudinal magnetization strength after relaxation is smoothest includes: for each nesting manner, calculating a mean value and a variance of the longitudinal magnetization strengths after relaxation of all slices when scanning ends corresponding to the nesting manner; and selecting a nesting manner for which the mean value is largest and the variance is smallest as the nesting manner for which the longitudinal magnetization strength after relaxation is smoothest.

In an exemplary embodiment, the calculating the longitudinal magnetization strength after relaxation of each slice when scanning ends includes: when a scan is performed of any target slice, then for the target slice and each slice amongst slices suffering interference, based on a longitudinal magnetization strength after relaxation of the slice in a most recent scanning process and a flip angle of the slice in a current scanning process, calculating a longitudinal magnetization strength after flipping of the slice in the current scanning process, and calculating a longitudinal magnetization strength after relaxation of the slice in the current scanning process on the basis of the longitudinal magnetization strength after flipping of the slice in the current scanning process, where for any target slice, an echo profile obtained when a preset pulse is used to perform an MRI scan of the target slice is tested in advance, and slices suffering interference, and a flip angle of each slice suffering interference, are determined on the basis of the echo profile.

In an exemplary embodiment, the preset pulse sequence is a turbo spin echo (TSE) sequence.

In an exemplary embodiment, an apparatus for determining an optimal magnetic resonance imaging (MRI) scan nesting manner, includes: a selectable nesting manner determiner, a simulated scanner, and an optimal nesting manner calculator.

In an exemplary embodiment, the selectable nesting manner determiner is configured to determine all selectable nesting manners according to a preset number of simulated scan slices. In an exemplary embodiment, the selectable nesting manner determiner includes processor circuitry that is configured to perform one or more functions/operations of the selectable nesting manner determiner, including determining all selectable nesting manners.

In an exemplary embodiment, the simulated scanner is configured to: sequentially select one nesting manner from all the selectable nesting manners determined by the selectable nesting manner determiner; use a preset pulse sequence to perform a simulated MRI scan of a set tissue based on the selected nesting manner, and calculate a longitudinal magnetization strength after relaxation of each slice when scanning ends. In an exemplary embodiment, the simulated scanner includes processor circuitry that is configured to perform one or more functions/operations of the simulated scanner, including selecting nesting manners and calculated the longitudinal magnetization strength.

In an exemplary embodiment, the optimal nesting manner calculator is configured to: when all nesting manners have been selected, select a nesting manner for which the longitudinal magnetization strength after relaxation is smoothest, based on the longitudinal magnetization strength after relaxation of each slice when scanning ends corresponding to each nesting manner as calculated by the simulated scanner; and use the selected nesting manner as an optimal nesting manner for performing an MRI scan of the tissue. In an exemplary embodiment, the optimal nesting manner calculator includes processor circuitry that is configured to perform one or more functions/operations of the optimal nesting manner calculator, including selecting the nesting manner for which the longitudinal magnetization strength after relaxation is smoothest and using the selected nesting manner as the optimal nesting manner.

In an exemplary embodiment, the selectable nesting manner determiner, the simulated scanner, and the optimal nesting manner calculator are modules of a processor. In another embodiment, one or more of the selectable nesting manner determiner, the simulated scanner, and the optimal nesting manner calculator are included in separate processors.

In an exemplary embodiment, the determining all the selectable nesting manners by the selectable nesting manner determiner includes:

calculating M=⌊total number of scan slices/2⌋, where ⌊ ⌋ is a symbol for rounding down. Here, there are a total of M selectable nesting manners, where the smallest incremental number of slices corresponding to a selectable nesting manner=1, and the largest incremental number of slices=M.

In an exemplary embodiment, the selecting the nesting manner for which the longitudinal magnetization strength after relaxation is smoothest by the optimal nesting manner calculator includes: for each nesting manner, calculating a mean value and a variance of the longitudinal magnetization strengths after relaxation of all slices when scanning ends corresponding to the nesting manner; and selecting a nesting manner for which the mean value is largest and the variance is smallest as the nesting manner for which the longitudinal magnetization strength after relaxation is smoothest.

In an exemplary embodiment, the calculating the longitudinal magnetization strength after relaxation of each slice when scanning ends by the simulated scanner includes: when a scan is performed of any target slice, then for the target slice and each slice amongst slices suffering interference, based on a longitudinal magnetization strength after relaxation of the slice in a most recent scanning process and a flip angle of the slice in a current scanning process, calculating a longitudinal magnetization strength after flipping of the slice in the current scanning process, and calculating a longitudinal magnetization strength after relaxation of the slice in the current scanning process on the basis of the longitudinal magnetization strength after flipping of the slice in the current scanning process. In an exemplary embodiment, for any target slice, an echo profile obtained when a preset pulse is used to perform an MRI scan of the target slice is tested in advance, and slices suffering interference, and a flip angle of each slice suffering interference, are determined on the basis of the echo profile.

In an exemplary embodiment, the preset pulse sequence used by the simulated scanner is a turbo spin echo (TSE) sequence, but is not limited thereto.

In an exemplary embodiment, a computer-readable storage medium is provided. The computer-readable storage medium includes a computer program stored thereon; when executed by a processor, the processor performs one or more of the operations of any one of the methods for determining an optimal magnetic resonance imaging (MRI) scan nesting manner described herein. In an exemplary embodiment, the computer-readable storage medium is a memory storage device (e.g. memory, hard drive, solid-state memory, CD-ROM, or the like).

In an exemplary embodiment, an apparatus configured to determine an optimal magnetic resonance imaging (MRI) scan nesting manner includes a processor and a memory. The memory can store an application program executable by the processor, and causes the processor to perform one or more operations of any one of the methods for determining an optimal magnetic resonance imaging (MRI) scan nesting manner described herein.

Advantageously, by using each selectable nesting manner individually to perform a simulated MRI scan of tissue, and selecting the nesting manner for which the longitudinal magnetization strength is smoothest as the optimal nesting manner for performing an MRI scan of the tissue, the present disclosure finds the optimal MRI scan nesting manner.

FIG. 1 is a flow chart of a method for determining an optimal MRI scan nesting manner according to an exemplary embodiment of the present disclosure. In an exemplary embodiment, the method includes the following steps:

Step 101: determining all selectable MRI scan nesting manners according to a preset number of simulated scan slices.

Step 102: sequentially selecting one nesting manner from all the selectable nesting manners.

Step 103: using the selected nesting manner, using a preset pulse sequence to perform a simulated MRI scan of a set tissue, and calculating a longitudinal magnetization strength after relaxation of each slice when scanning ends.

Step 104: when all nesting manners have been selected, then based on the longitudinal magnetization strength after relaxation when scanning ends corresponding to each nesting manner, selecting a nesting manner for which the longitudinal magnetization strength after relaxation when scanning ends is smoothest, and using this nesting manner as an optimal nesting manner for performing an MRI scan of the tissue.

Figure 2:
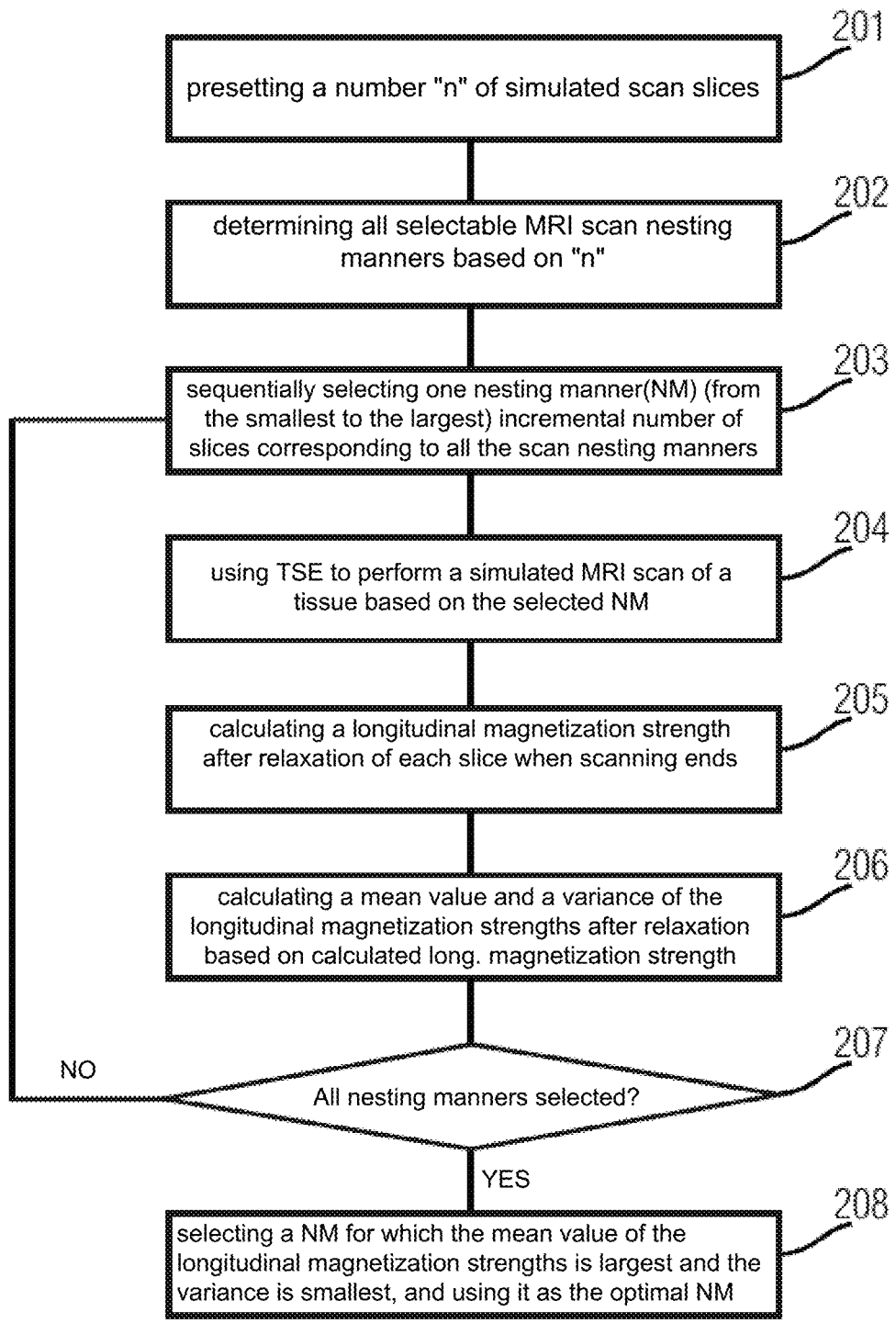
FIG. 2 is a flow chart of a method for determining an optimal MRI scan nesting manner according to an exemplary embodiment of the present disclosure.

FIG. 2 is a flow chart of a method for determining an optimal MRI scan nesting manner according to an exemplary embodiment of the present disclosure. In an exemplary embodiment, the method include the following steps:

Step 201: presetting a number n of simulated scan slices.

This embodiment only simulates an MRI scanning process, and thereby calculates the optimal MRI scan nesting manner; it does not really perform an MRI scanning process.

Step 202: determining all selectable MRI scan nesting manners according to the number n of simulated scan slices.

Each nesting manner corresponds to an incremental number of slices, with the smallest incremental number of slices=1, and in general, the largest incremental number of slices M=⌊total number of scan slices/2⌋, where ⌊ ⌋ is the symbol for rounding down, so that there are a total of M selectable MRI scan nesting manners.

Step 203: sequentially selecting one nesting manner, in order from the smallest to the largest incremental number of slices corresponding to all the selectable MRI scan nesting manners.

Step 204: using the selected nesting manner, using TSE to perform a simulated MRI scan of a tissue.

Step 205: calculating a longitudinal magnetization strength after relaxation of each slice when scanning ends.

When a scan is performed of any target slice, then for the target slice and each slice amongst slices suffering interference, based on a longitudinal magnetization strength after relaxation of the slice in a most recent scanning process and a flip angle of the slice in a current scanning process, a longitudinal magnetization strength after flipping of the slice in the current scanning process is calculated, and a longitudinal magnetization strength after relaxation of the slice in the current scanning process is calculated on the basis of the longitudinal magnetization strength after flipping of the slice in the current scanning process;

it must be explained that when a 90° excitation pulse or a 180° refocusing pulse is used to scan a target slice, adjacent slices of the target slice will also be scanned, thereby generating an echo signal of a different strength; these adjacent slices are called slices suffering interference, and flip angles of slices suffering interference can be determined by testing in advance. Specifically, for each target slice, an echo profile obtained when a corresponding TSE pulse is used to perform an MRI scan of the target slice is tested in advance, and slices suffering interference, and the flip angle of each slice suffering interference, are determined on the basis of the echo profile.

Specifically, for a target slice and each of the slices suffering interference, the longitudinal magnetization strength after relaxation of the slice in the current scanning process is calculated by the following two formulae:

Longitudinal magnetization strength after flipping of the slice in the current scanning process=longitudinal magnetization strength after relaxation of the slice in the previous scanning process $*\cos\theta$, wherein $\theta$ is the flip angle of the slice in the current scanning process;

longitudinal magnetization strength after relaxation of the slice in the current scanning process=longitudinal magnetization strength after flipping of the slice in the current scanning process $*e^{-\Delta t/T1}+M0*(1-e^{-\Delta t/T1})$, wherein T1 is the longitudinal relaxation time of the tissue, and $\Delta t$ is echo spacing, $\Delta t=TR/n/ETL$, n being the number of scan slices.

Figure 3:
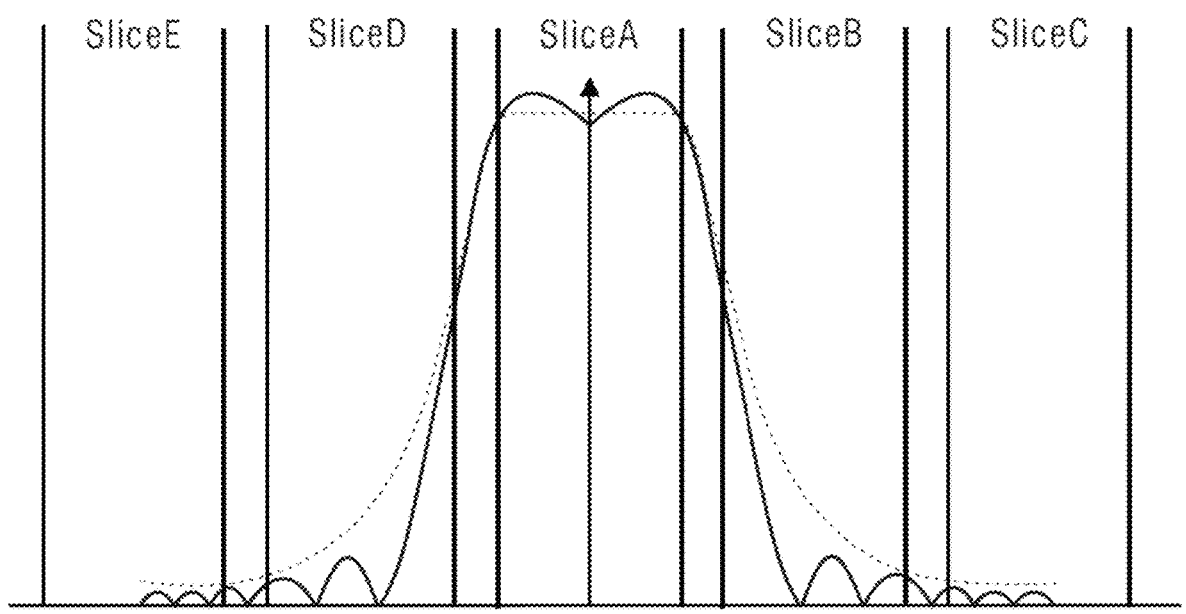
FIG. 3 is a diagram of adjacent slices suffering interference when a target slice (e.g. SliceA) is scanned.

FIG. 3 shows a schematic diagram of adjacent slices suffering interference when a target slice, SliceA, is scanned. In this example, the solid curve in the figure represents a real echo profile, whereas the dotted curve represents an echo profile obtained by fitting. Clearly, when SliceA is scanned, SliceB, SliceC, SliceD and SliceE all generate an echo, and the strength of the echo signal is gradually attenuated as the distance from SliceA increases; the flip angles of SliceB, SliceC, SliceD and SliceE in the current scanning process can be obtained through measurement of the dotted curve.

Step 206: based on the calculated longitudinal magnetization strength after relaxation of each slice when scanning ends, calculating a mean value and a variance of the longitudinal magnetization strengths after relaxation of all slices when scanning ends.

Step 207: determining whether all nesting manners have been selected, and if so, performing step 208: otherwise, returning to step 203.

Step 208: based on the mean value and variance of the longitudinal magnetization strengths after relaxation of all slices when scanning ends corresponding to each nesting manner, selecting a nesting manner for which the mean value of the longitudinal magnetization strengths is largest and the variance is smallest, and using this nesting manner as an optimal nesting manner.

If the longitudinal magnetization strengths after relaxation of all slices when scanning ends corresponding to a nesting manner have the largest mean value but not the smallest variance, then the two nesting manners with the foremost mean values are selected, and the nesting manner with the smaller variance is selected from these two nesting manners as the optimal nesting manner.

Subsequently, in an actual application, when performing an MRI scan of this type of tissue, the optimal nesting manner is used to perform the MRI scan of the tissue.

In an actual application, for each type of tissue, steps 101-104 or 201-208 described above may be performed once, to find the optimal nesting manner for performing an MRI scan of this type of tissue.

The steps/operations of the methods illustrated in FIGS. 1 and 2 can be performed in a different order than shown. Further two or more steps/operations can be performed simultaneously.

A particular application example is given below:

An optimal MRI scan nesting manner for a tissue is to be sought. Let the total number of scan slices be n=10, then the incremental numbers of slices of the selectable nesting manners may be 1, 2, 3, 4 and 5, i.e. the slice scanning orders of the 5 corresponding nesting manners are as follows:

1) 1, 2, 3, 4, 5, 6, 7, 8, 9, 10;
2) 1, 3, 5, 7, 9, 2, 4, 6, 8, 10;
3) 1, 4, 7, 10, 2, 5, 8, 3, 6, 9;
4) 1, 5, 9, 2, 6, 10, 3, 7, 4, 8;
5) 1, 6, 2, 7, 3, 8, 4, 9, 5, 10.

First of all, nesting manner 1) 1, 2, 3, 4, 5, 6, 7, 8, 9, 10 is used to perform a simulated MRI scan of the tissue, then nesting manner 2) 1, 3, 5, 7, 9, 2, 4, 6, 8, 10 is used to perform a simulated MRI scan of the tissue, and so on, until simulated scans have been completed for all 5 nesting manners.

Taking as an example the case where TSE is used and nesting manner 2) 1, 3, 5, 7, 9, 2, 4, 6, 8, 10 is used to perform a simulated MRI scan, the specific process is as follows:

Step 01, using a 90° excitation pulse to perform a simulated scan of a 1st scan slice, i.e. slice 1; if it is found, on the basis of an echo profile curve obtained by testing in advance when a 90° excitation pulse is used to scan slice 1, that: when slice 1 is scanned, the flip angles of slices 2 and 3 are $\theta_{21}$ and $\theta_{31}$ respectively, and other slices do not suffer interference, then:

longitudinal magnetization strength after first flipping of slice 1=$M0$*cos 90°;

longitudinal magnetization strength after first flipping of slice 2=$M0$*cos $\theta_{21}$;

longitudinal magnetization strength after first flipping of slice 3=$M0$*cos $\theta_{31}$;

longitudinal magnetization strength after first relaxation of slice 1=longitudinal magnetization strength after first flipping of slice 1*$e^{-\Delta t/T1}$+$M0$*$(1-e^{-\Delta t/T1})$;

longitudinal magnetization strength after first relaxation of slice 2=longitudinal magnetization strength after first flipping of slice 2*$e^{-\Delta t/T1}$+$M0$*$(1-e^{-\Delta t/T1})$;

longitudinal magnetization strength after first relaxation of slice 3=longitudinal magnetization strength after first flipping of slice 3*$e^{-\Delta t/T1}$+$M0$*$(1-e^{-\Delta t/T1})$;

wherein M0 is the value of longitudinal magnetization strength in an equilibrium state, generally let M0=1, T1 is the longitudinal relaxation time of the tissue, and $\Delta t$ is the echo spacing, $\Delta t$=TR/n/ETL, n being the number of scan slices.

Step 02, using a 180° refocusing pulse to perform a simulated scan of a 2nd scan slice, i.e. slice 3; if it is found, on the basis of an echo profile curve obtained by testing in advance when a 180° refocusing pulse is used to scan slice 3, that: the flip angles of slices 1, 2, 4 and 5 are $\theta_{13}$, $\theta_{23}$, $\theta_{43}$, and $\theta_{53}$ respectively, and other slices do not suffer interference, then:

longitudinal magnetization strength after second flipping of slice 3=longitudinal magnetization strength after first relaxation of slice 3*cos 180°;

longitudinal magnetization strength after second flipping of slice 1=longitudinal magnetization strength after first relaxation of slice 1*cos $\theta_{13}$;

longitudinal magnetization strength after second flipping of slice 2=longitudinal magnetization strength after first relaxation of slice 2*cos $\theta_{23}$;

longitudinal magnetization strength after first flipping of slice 4=$M0$*cos $\theta_{43}$;

longitudinal magnetization strength after first flipping of slice 5=$M0$*cos $\theta_{53}$;

longitudinal magnetization strength after second relaxation of slice 3=longitudinal magnetization strength after second flipping of slice 3*$e^{-\Delta t/T1}$+$M0$*$(1-e^{-\Delta t/T1})$;

longitudinal magnetization strength after second relaxation of slice 1=longitudinal magnetization strength after second flipping of slice 1*$e^{-\Delta t/T1}$+$M0$*$(1-e^{-\Delta t/T1})$;

longitudinal magnetization strength after second relaxation of slice 2=longitudinal magnetization strength after second flipping of slice 2*$e^{-\Delta t/T1}$+$M0$*$(1-e^{-\Delta t/T1})$;

longitudinal magnetization strength after first relaxation of slice 4=longitudinal magnetization strength after first flipping of slice 4*$e^{-\Delta t/T1}$+$M0$*$(1-e^{-\Delta t/T1})$;

longitudinal magnetization strength after first relaxation of slice 5=longitudinal magnetization strength after first flipping of slice 5*$e^{-\Delta t/T1}$+$M0$*$(1-e^{-\Delta t/T1})$.

Step 03, using a 180° refocusing pulse to perform a simulated scan of a 3rd scan slice, i.e. slice 5; if it is found, on the basis of an echo profile curve obtained by testing in advance when a 180° refocusing pulse is used to scan slice 5, that: the flip angles of slices 3, 4, 6 and 7 are $\theta_{35}$, $\theta_{45}$, $\theta_{65}$ and $\theta_{75}$ respectively, and other slices do not suffer interference, then:

longitudinal magnetization strength after second flipping of slice 5=longitudinal magnetization strength after first relaxation of slice 5*cos 180°;

longitudinal magnetization strength after third flipping of slice 3=longitudinal magnetization strength after second relaxation of slice 3*cos $\theta_{35}$;

longitudinal magnetization strength after second flipping of slice 4=longitudinal magnetization strength after first relaxation of slice 4*cos $\theta_{45}$;

longitudinal magnetization strength after first flipping of slice 6=$M0$*cos $\theta_{65}$;

longitudinal magnetization strength after first flipping of slice 7=$M0$*cos $\theta_{75}$;

longitudinal magnetization strength after second relaxation of slice 5=longitudinal magnetization strength after second flipping of slice 5*$e^{-\Delta t/T1}$+$M0$*(1-$e^{-\Delta t/T1}$);

longitudinal magnetization strength after third relaxation of slice 3=longitudinal magnetization strength after third flipping of slice 3*$e^{-\Delta t/T1}$+$M0$*(1-$e^{-\Delta t/T1}$);

longitudinal magnetization strength after second relaxation of slice 4=longitudinal magnetization strength after second flipping of slice 4*$e^{-\Delta t/T1}$+$M0$*(1-$e^{-\Delta t/T1}$);

longitudinal magnetization strength after first relaxation of slice 6=longitudinal magnetization strength after first flipping of slice 6*$e^{-\Delta t/T1}$+$M0$*(1-$e^{-\Delta t/T1}$);

longitudinal magnetization strength after first relaxation of slice 7=longitudinal magnetization strength after first flipping of slice 7*$e^{-\Delta t/T1}$+$M0$*(1-$e^{-\Delta t/T1}$).

Step 04, using a 180° refocusing pulse to perform a simulated scan of a 4th scan slice, i.e. slice 7.

The processes of calculating the longitudinal magnetization strength for the flipping and relaxation processes of the target slice and the slices suffering interference are the same as above, so are not described again superfluously.

Step 10, using a 180° refocusing pulse to perform a simulated scan of a 10th scan slice, i.e. slice 10.

The processes of calculating the longitudinal magnetization strength for the flipping and relaxation processes of the target slice and the slices suffering interference are the same as above, so are not described again superfluously.

At this point, the current simulated scan process ends; the longitudinal magnetization strength after relaxation of each slice under nesting manner 2) is obtained, and the mean value and variance of the longitudinal magnetization strengths after relaxation of all slices corresponding to nesting manner 2) are calculated.

When simulated scans have been completed for all 5 nesting manners, then based on the mean value and variance of the longitudinal magnetization strengths after relaxation of all layers corresponding to the 5 nesting manners, the nesting manner for which the mean value is largest and the variance is smallest is found therefrom as the optimal nesting manner.

Figure 4:
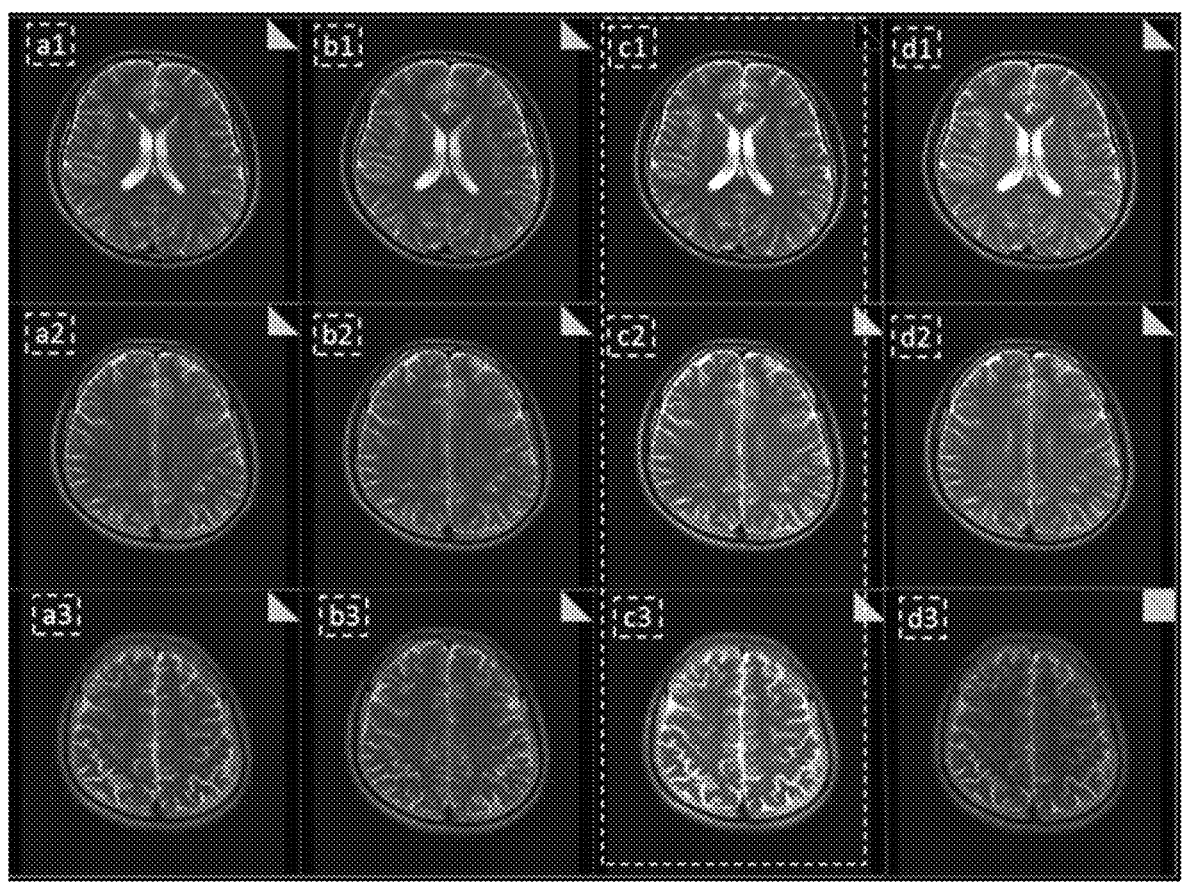
FIG. 4 illustrates example MRI scans of a human brain provided from a method to determine an optimal MRI scan nesting manner according to an exemplary embodiment of the present disclosure.

FIG. 4 is an example of using the method of the present disclosure to perform an MRI scan of a human brain, and determining an optimal MRI scan nesting manner, wherein:

A 1.5T MRI scanner (e.g. Siemens Healthineers, Shenzhen, China) and a 16-channel head/neck coil are used to perform T2 brain imaging; the pulse sequence is a TSE sequence, and the protocol parameters are as follows: FOV (field of view)=208×230 mm, TR=4700 ms, TE=84 ms, ETL=21, BW (bandwidth)/pixel=190 HZ, number of scan slices=20, distance factor=30%, voxel=0.4×0.4×5 mm, TA (total scan time)=2:35'.

Figs. a1-a3 are MRI images obtained using a nesting manner with an increment of 1;

figs. b1-b3 are MRI images obtained using a nesting manner with an increment of 3;

figs. c1-c3 are MRI images obtained using a nesting manner with an increment of 4;

figs. d1-d3 are MRI images obtained using a nesting manner with an increment of 6.

As can be seen, the MRI images obtained using a nesting manner with an increment of 4 are optimal.

Figure 5:
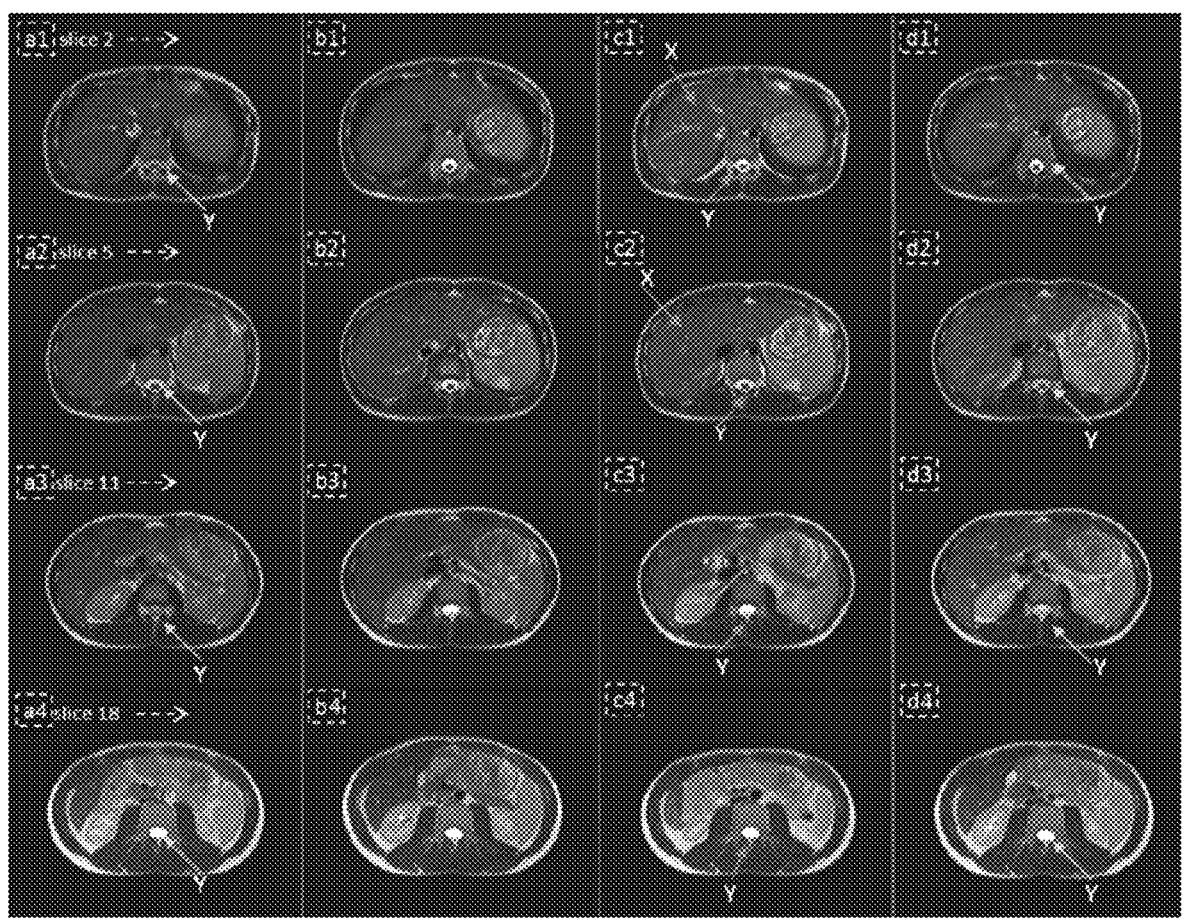
FIG. 5 illustrates example MRI scans of a human abdomen provided from a method to determine an optimal MRI scan nesting manner according to an exemplary embodiment of the present disclosure.

FIG. 5 is an example of using the method of the present disclosure to perform an MRI scan of a human abdomen, and determining an optimal MRI scan nesting manner, wherein:

A 1.5T MRI scanner (e.g. Siemens Healthineers, Shenzhen, China) and a 13-channel body matrix coil are used to perform T2 abdomen imaging; the pulse sequence is a haste sequence, (two breath-holds) and the protocol parameters are as follows: FOV=380×309 mm, TE/TR=91/1000 ms, BW/pixel=700 Hz, number of scan slices=30, distance factor=20%, voxel=1.5×1.5×6 mm, TA=35'.

Figs. a1-a4 are MRI images obtained using a nesting manner with an increment of 1;

figs. b1-b4 are MRI images obtained using a nesting manner with an increment of 3;

figs. c1-c4 are MRI images obtained using a nesting manner with an increment of 4;

figs. d1-d4 are MRI images obtained using a nesting manner with an increment of 6;

figs. a1, b1, c1 and d1 are MRI images obtained by scanning Slice 2; figs. a2, b2, c2 and d2 are MRI images obtained by scanning Slice 5; figs. a3, b3, c3 and d3 are MRI images obtained by scanning Slice 11; figs. a4, b4, c4 and d4 are MRI images obtained by scanning Slice 18.

The X arrows in the figures point to the liver; as can be seen, the contrast between the liver and blood vessels is most apparent in figs. c1-c2;

the Y arrows in the figures point to cerebrospinal fluid of the abdomen; as can be seen, the signal strength of cerebrospinal fluid is highest and uniform in figs. c1-c4, while the signal strength of cerebrospinal fluid is weaker and not uniform in figs. a1-a4 and figs. d1-d4.

It can thus be seen that the MRI images obtained using the standard nesting manner, i.e. the nesting manner with an increment of 1, have poor contrast, so this is not the optimal nesting manner. The MRI images obtained using the nesting manner with an increment of 4 have obvious contrast, with the highest signal strength which is also uniform; this is the optimal nesting manner.

Figure 6:
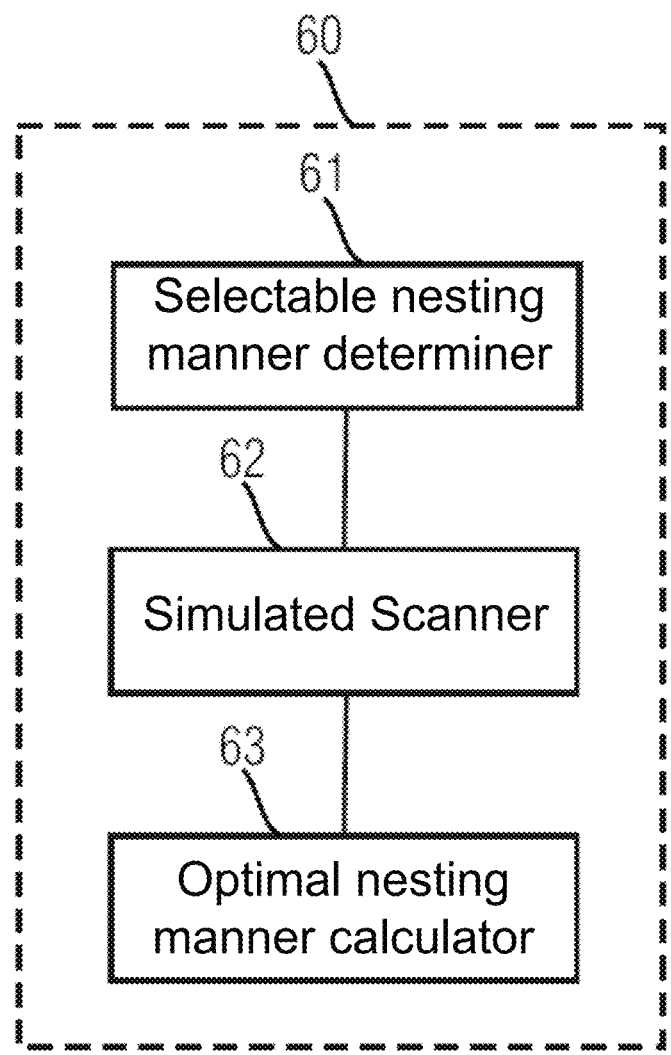
FIG. 6 is a schematic illustration of an apparatus for determining an optimal MRI scan nesting manner according to an exemplary embodiment of the present disclosure.

FIG. 6 is a schematic diagram of an apparatus 60 according to an exemplary embodiment. The apparatus 60 is configured to determine an optimal MRI scan nesting manner. In an exemplary embodiment, the apparatus 60 includes a selectable nesting manner determiner 61, a simulated scanner 62 and an optimal nesting manner calculator 63.

In an exemplary embodiment, the selectable nesting manner determiner 61 is configured to determine all selectable nesting manners according to a preset number of simulated scan slices. In an exemplary embodiment, the selectable nesting manner determiner 61 includes processor circuitry that is configured to perform one or more functions/operations of the selectable nesting manner determiner 61, including determining all selectable nesting manners.

In an exemplary embodiment, the simulated scanner 62 is configured to: sequentially select one nesting manner from all the selectable nesting manners determined by the selectable nesting manner determiner 61; using the selected nesting manner, uses a preset pulse sequence to perform a simulated MRI scan of a set tissue; and calculate a longitudinal magnetization strength after relaxation of each slice when scanning ends. In an exemplary embodiment, the simulated scanner 62 includes processor circuitry that is configured to perform one or more functions/operations of the simulated scanner 62, including selecting nesting manners and calculated the longitudinal magnetization strength.

In an exemplary embodiment, the optimal nesting manner calculator 63 is configured to: when all nesting manners have been selected, select a nesting manner for which the longitudinal magnetization strength after relaxation is smoothest, based on the longitudinal magnetization strength after relaxation of each slice when scanning ends corresponding to each nesting manner as calculated by the simulated scanner 62; and use this nesting manner as an optimal nesting manner for performing an MRI scan of the tissue. In an exemplary embodiment, the optimal nesting manner calculator 63 includes processor circuitry that is configured to perform one or more functions/operations of the optimal nesting manner calculator 63, including selecting the nesting manner for which the longitudinal magnetization strength after relaxation is smoothest and using the selected nesting manner as the optimal nesting manner.

In an exemplary embodiment, the selectable nesting manner determiner 61, the simulated scanner 62, and the optimal nesting manner calculator 63 are modules of a processor. In another embodiment, one or more of the selectable nesting manner determiner 61, the simulated scanner 62, and the optimal nesting manner calculator 63 are included in separate processors.

In an exemplary embodiment, determining all selectable nesting manners by the selectable nesting manner determiner 61 includes:

calculating M=⌊total number of scan slices/2⌋, where ⌊ ⌋ is the symbol for rounding down; then there are a total of M selectable nesting manners, wherein the smallest incremental number of slices corresponding to a selectable nesting manner=1, and the largest incremental number of slices=M.

In an exemplary embodiment, the selecting the nesting manner for which the longitudinal magnetization strength after relaxation is smoothest by the optimal nesting manner calculator 63 includes: for each nesting manner, calculating a mean value and a variance of the longitudinal magnetization strengths after relaxation of all slices when scanning ends corresponding to the nesting manner; and selecting a nesting manner for which the mean value is largest and the variance is smallest as the nesting manner for which the longitudinal magnetization strength after relaxation is smoothest.

In an exemplary embodiment, the calculating the longitudinal magnetization strength after relaxation of each slice when scanning ends by the simulated scanner 62 includes: when a scan is performed of any target slice, then for the target slice and each slice amongst slices suffering interference, based on a longitudinal magnetization strength after relaxation of the slice in a most recent scanning process and a flip angle of the slice in a current scanning process, calculating a longitudinal magnetization strength after flipping of the slice in the current scanning process, and calculating a longitudinal magnetization strength after relaxation of the slice in the current scanning process on the basis of the longitudinal magnetization strength after flipping of the slice in the current scanning process, where for any target slice, an echo profile obtained when a preset pulse is used to perform an MRI scan of the target slice is tested in advance, and slices suffering interference, and the flip angle of each slice suffering interference, are determined on the basis of the echo profile.

In an exemplary embodiment, a preset pulse sequence used by the simulated scanner 62 is TSE, but is not limited thereto.

Figure 7:
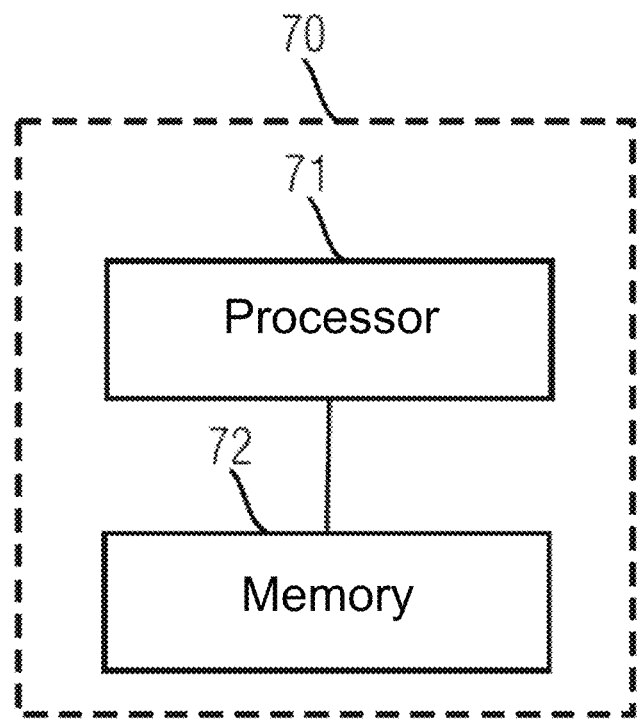
FIG. 7 is a schematic illustration of an apparatus for determining an optimal MRI scan nesting manner according to an exemplary embodiment of the present disclosure.

FIG. 7 is a schematic composition diagram of an apparatus 70 according to an exemplary embodiment, for determining an optimal MRI scan nesting manner. In an exemplary embodiment, the apparatus 70 includes a processor 71 and a memory 72.

In an exemplary embodiment, the memory 72 stores an application program executable by the processor 71, which causes the processor 71 to perform one or more of the steps/operations of the method for determining an optimal MRI scan nesting manner as described in any one of steps 101-104 or 201-208.

Embodiments of the present disclosure also provide a computer-readable storage medium, with a computer program stored thereon; when executed by a processor, the computer program realizes a step of the method for determining an optimal MRI scan nesting manner as described in any one of steps 101-104 or 201-208.

A machine-readable instruction is stored on the readable storage medium; the machine-readable instruction, when executed by a processor, causes the processor to perform any one of the methods described above. Specifically, a system or apparatus equipped with a readable storage medium may be provided; software program code realizing a function of any one of the embodiments above is stored on the readable storage medium, and a computer or processor of the system or apparatus is caused to read and execute a machine-readable instruction stored in the readable storage medium.

In such a situation, program code read from the readable storage medium can itself realize a function of any one of the embodiments above, hence machine-readable code and the readable storage medium storing the machine-readable code form part of the present disclosure.

Examples of readable storage media include floppy disks, hard disks, magneto-optical disks, optical disks (such as CD-ROM, CD-R, CD-RW, DVD-ROM, DVD-RAM, DVD-RW, DVD+RW), magnetic tapes, non-volatile memory cards and ROM. Optionally, program code may be downloaded from a server computer or a cloud via a communication network.

Those skilled in the art should understand that various changes in form and amendments may be made to the embodiments disclosed above without deviating from the substance of the disclosure. Thus, the scope of protection of the present disclosure shall be defined by the attached claims.

It must be explained that not all of the steps and modules in the flows and system structure diagrams above are necessary; certain steps or modules may be omitted according to actual requirements. The order in which steps are executed is not fixed, but may be adjusted as required. The apparatus structures described in the embodiments above may be physical structures, and may also be logical structures, i.e. some modules might be realized by the same physical entity, or some modules might be realized by multiple physical entities, or realized jointly by certain components in multiple independent devices.

In the embodiments above, a hardware module may be realized in a mechanical or an electrical manner. For example, a hardware module or processor may include a permanent dedicated circuit or logic (e.g. a special processor, FPGA or ASIC) to complete a corresponding operation. A hardware module or processor may also include programmable logic or circuitry (e.g. a universal processor or another programmable processor), and may be set temporarily by software to complete a corresponding operation. Particular embodiments (mechanical, or dedicated permanent circuitry, or temporarily set circuitry) may be determined on the basis of considerations of cost and time.

The present disclosure has been displayed and explained in detail above by means of the accompanying drawings and preferred embodiments, but the present disclosure is not limited to these disclosed embodiments. Based on the embodiments described above, those skilled in the art will know that further embodiments of the present disclosure, also falling within the scope of protection of the present disclosure, could be obtained by combining code checking means in different embodiments above.

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure.

Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

101-104 steps
201-208 steps
60 apparatus
61 selectable nesting manner determiner
62 simulated scanner
63 optimal nesting manner calculator
70 apparatus
71 processor
72 memory

The invention claimed is:

1. A method for determining an optimal magnetic resonance imaging (MRI) scan nesting manner, the method comprising:
   determining selectable nesting manners according to a preset number of simulated scan slices;
   sequentially selecting one nesting manner from the selectable nesting manners;
   performing a simulated MRI scan of a set tissue based on the selected nesting manner and using a preset pulse sequence;
   calculating a longitudinal magnetization strength after relaxation of each slice following the simulated MRI scan;
   when all determined nesting manners have been selected, selecting, based on the longitudinal magnetization strength after relaxation of each slice corresponding to each nesting manner, a nesting manner from the determined nesting manners having a smoothest longitudinal magnetization strength after relaxation; and providing the selected nesting manner, as an optimal nesting manner for performing an MRI scan of the tissue, as an output data file.

2. The method as claimed in claim 1, wherein determining the selectable nesting manners comprises:

calculating M=⌊total number of scan slices/2⌋ wherein ⌊ ⌋ is a rounding down function and M is a total of selectable nesting manners; and wherein a smallest incremental number of slices corresponding to a selectable nesting manner=1, and a largest incremental number of slices=M.

3. The method as claimed in claim 1, wherein selecting the nesting manner for which the longitudinal magnetization strength after relaxation is smoothest comprises:

for each nesting manner of the determined nesting manners, calculating a mean value and a variance of the longitudinal magnetization strengths after relaxation of all slices when scanning ends corresponding to the nesting manner; and selecting a nesting manner for which the mean value is largest and the variance is smallest as the nesting manner for which the longitudinal magnetization strength after relaxation is smoothest.

4. The method as claimed in claim 1, wherein calculating the longitudinal magnetization strength after relaxation of each slice comprises:

when a scan is performed of any target slice, for the target slice and each slice amongst slices suffering interference, based on a longitudinal magnetization strength after relaxation of the slice in a most recent scanning process and a flip angle of the slice in a current scanning process:

calculating a longitudinal magnetization strength after flipping of the slice in a current scanning process; and calculating a longitudinal magnetization strength after relaxation of the slice in the current scanning process on the basis of the longitudinal magnetization strength after flipping of the slice in the current scanning process, wherein:

for the any target slice, an echo profile obtained when a preset pulse is used to perform an MRI scan of the target slice is tested in advance, and based on the echo profile, slices suffering interference and a flip angle of each slice suffering interference are determined.

5. The method as claimed in claim 1, wherein the preset pulse sequence is a turbo spin echo (TSE) sequence.

6. The method as claimed in claim 1, further comprising controlling an MRI scanner to perform the MRI scan of the tissue based on the output data file corresponding to the optimal nesting manner.

7. The method as claimed in claim 1, further comprising performing the MRI scan, using an MRI scanner, based on the output data file corresponding to the optimal nesting manner.

8. A non-transitory computer-readable storage medium, with a computer program stored thereon, that when executed by a processor, instructs the processor to perform the method as claimed in claim 1.

9. An apparatus for determining an optimal magnetic resonance imaging (MRI) scan nesting manner, the apparatus comprising:

a selectable nesting manner determiner configured to determine selectable nesting manners according to a preset number of simulated scan slices;

a simulated scanner configured to:

sequentially select a nesting manner from the determined selectable nesting manners;

based on the selected nesting manner, performing a simulated MRI scan of a set tissue using a preset pulse sequence; and calculate a longitudinal magnetization strength after relaxation of each slice when scanning ends; and an optimal nesting manner calculator configured to:

when all of the selectable nesting manners have been selected, select a nesting manner from the selectable nesting manners having a smoothest longitudinal magnetization strength after relaxation, based on the calculated longitudinal magnetization strength after relaxation of each slice corresponding to each nesting manner; and providing this nesting manner as an optimal nesting manner for performing an MRI scan of the tissue.

10. The apparatus as claimed in claim 9, wherein determining the selectable nesting manners by the selectable nesting manner determiner comprises:

calculating M=⌊total number of scan slices/2⌋ wherein ⌊ ⌋ is a rounding down function; and wherein a smallest incremental number of slices corresponding to a selectable nesting manner=1, and a largest incremental number of slices=M.

11. The apparatus as claimed in claim 9, wherein selecting the nesting manner for which the longitudinal magnetization strength after relaxation is smoothest by the optimal nesting manner calculator comprises:

for each nesting manner of the determined nesting manners, calculating a mean value and a variance of the longitudinal magnetization strengths after relaxation of all slices when scanning ends corresponding to the nesting manner; and selecting a nesting manner for which the mean value is largest and the variance is smallest as the nesting manner for which the longitudinal magnetization strength after relaxation is smoothest.

12. The apparatus as claimed in claim 9, wherein calculating the longitudinal magnetization strength after relaxation of each slice comprises:

when a scan is performed of any target slice, for the target slice and each slice amongst slices suffering interference, based on a longitudinal magnetization strength after relaxation of the slice in a most recent scanning process and a flip angle of the slice in a current scanning process:

calculating a longitudinal magnetization strength after flipping of the slice in a current scanning process, and calculating a longitudinal magnetization strength after relaxation of the slice in the current scanning process on the basis of the longitudinal magnetization strength after flipping of the slice in the current scanning process, wherein:

for any target slice, an echo profile obtained when a preset pulse is used to perform an MRI scan of the target slice is tested in advance, and based on the echo profile, slices suffering interference, and a flip angle of each slice suffering interference, are determined.

13. The apparatus as claimed in claim 9, wherein the preset pulse sequence used by the simulated scanner is a turbo spin echo (TSE) sequence.

14. The method as claimed in claim 1, wherein the nesting manner for which the longitudinal magnetization strength after relaxation is smoothest is a nesting manner of the determined nesting manners having a largest mean value and smallest variance of corresponding mean values and variances of the determined nesting manners.

15. An apparatus for determining an optimal magnetic resonance imaging (MRI) scan nesting manner, the apparatus comprising:

a memory storing an application program; and a processor configured to execute the application program to cause the processor to:

determine selectable nesting manners according to a preset number of simulated scan slices;

sequentially select one nesting manner from the selectable nesting manners;

perform a simulated MRI scan of a set tissue based on the selected nesting manner and using a preset pulse sequence;

calculate a longitudinal magnetization strength after relaxation of each slice following the simulated MRI scan;

when all determined nesting manners have been selected, select, based on the longitudinal magnetization strength after relaxation of each slice corresponding to each nesting manner, a nesting manner from the determined nesting manners having a smoothest longitudinal magnetization strength after relaxation; and provide the selected nesting manner, as an optimal nesting manner for performing an MRI scan of the tissue, as an output data file.

* * * * *